United States Patent
Hsia

(10) Patent No.: US 9,913,872 B2
(45) Date of Patent: Mar. 13, 2018

(54) DIABETIC NUTRITIONAL COMPOSITION

(71) Applicant: Houn Simon Hsia, Irvine, CA (US)

(72) Inventor: Houn Simon Hsia, Irvine, CA (US)

(73) Assignee: Houn Simon Hsia, Irvine, CA (US)

( * ) Notice: Subject to any disclaimer, the term of this patent is extended or adjusted under 35 U.S.C. 154(b) by 575 days.

(21) Appl. No.: 14/045,920

(22) Filed: Oct. 4, 2013

(65) Prior Publication Data

US 2015/0098930 A1    Apr. 9, 2015

(51) Int. Cl.

| | |
|---|---|
| *A61K 36/8998* | (2006.01) |
| *A61K 31/015* | (2006.01) |
| *A61K 31/047* | (2006.01) |
| *A61K 31/122* | (2006.01) |
| *A61K 31/353* | (2006.01) |
| *A61K 31/4415* | (2006.01) |
| *A61K 31/519* | (2006.01) |
| *A61K 31/593* | (2006.01) |
| *A61K 31/733* | (2006.01) |
| *A61K 33/04* | (2006.01) |
| *A61K 33/24* | (2006.01) |
| *A61K 33/30* | (2006.01) |
| *A61K 36/42* | (2006.01) |
| *A61K 36/48* | (2006.01) |
| *A61K 36/899* | (2006.01) |
| *A61K 31/05* | (2006.01) |
| *A61K 31/375* | (2006.01) |
| *A61K 31/7004* | (2006.01) |
| *A61K 31/714* | (2006.01) |
| *A61K 36/752* | (2006.01) |

(52) U.S. Cl.
CPC ........ *A61K 36/8998* (2013.01); *A61K 31/015* (2013.01); *A61K 31/047* (2013.01); *A61K 31/05* (2013.01); *A61K 31/122* (2013.01); *A61K 31/353* (2013.01); *A61K 31/375* (2013.01); *A61K 31/4415* (2013.01); *A61K 31/519* (2013.01); *A61K 31/593* (2013.01); *A61K 31/7004* (2013.01); *A61K 31/714* (2013.01); *A61K 31/733* (2013.01); *A61K 33/04* (2013.01); *A61K 33/24* (2013.01); *A61K 33/30* (2013.01); *A61K 36/42* (2013.01); *A61K 36/48* (2013.01); *A61K 36/752* (2013.01); *A61K 36/899* (2013.01)

(58) Field of Classification Search
None
See application file for complete search history.

(56) References Cited

U.S. PATENT DOCUMENTS

| | | | |
|---|---|---|---|
| 7,879,796 B2 * | 2/2011 | Edens | A61K 31/198 |
| | | | 514/6.8 |
| 2010/0074969 A1 * | 3/2010 | Hughes | A23L 1/293 |
| | | | 424/655 |

OTHER PUBLICATIONS

Schrauzer (Pure Appl. Chem. (2006), vol. 78, No. 1, pp. 105-109).*

* cited by examiner

*Primary Examiner* — Susan C Hoffman
(74) *Attorney, Agent, or Firm* — Fish IP Law, LLC

(57) ABSTRACT

The present invention provides nutritional compositions as powders, lozenges, tablets or liquids that are employed as oral supplementation to the human diet. The compositions of the present invention provide for supplementation to the diet of the human system, and specifically for those humans predisposed to, or suffering from, the diabetic human condition. It is believed that the key ingredients of the present invention work synergistically together to aid in the slowing, stopping, or reversing the symptoms and metabolic disorder characteristic of the human diabetic condition. These essential components are comprised of uniquely-selected minerals, phytonutrients and vitamin combinations.

19 Claims, No Drawings

DIABETIC NUTRITIONAL COMPOSITION

FIELD OF THE INVENTION

The present invention relates to nutritional compositions useful for treatment of the diabetic condition in humans.

BACKGROUND OF THE INVENTION

Diabetes is one of the most deadly diseases of all mankind. Preventing and treatment of diabetes, therefore, and extremely important endeavor for mankind to pursue. Much progress has been made over the last 50 years for the treatment of diabetes, including dietary understanding of the disease, as well as a number of drug therapies. A major shortcoming of these therapeutic treatments is their harmful effects to the human system since, in many cases, the practice of such therapies causes the subject harm.

A healthy and potent human immune system and human endocrine system are salient to prevent and remediate the effects of the diabetic conditions. The preset invention overcomes many of the shortcomings of the prior art in connection with the preventative and remedial treatments of the diabetic human condition by providing compositions that work together in a synergistic manner, to enhance the endocrine system; and more specifically to prevent or slow down complications characteristic of the human diabetic condition.

SUMMARY OF THE INVENTION

The present invention provides nutritional compositions as powders, lozenges, tablets or liquids, that are employed as oral supplementation to the human diet. The compositions of the present invention provide for supplementation to the diet of the human system, and specifically for those humans predisposed to, or suffering from, the diabetic human condition.

It is the prime objective of the present invention to provide nutritive compositions that provide for an increased activity in combating the human diabetic condition.

It is another objective of the present invention to provide for compositions to treat the diabetic human condition, and help to reverse the symptoms of the diabetic condition.

It is another objective of the present invention to provide for compositions to prevent the diabetic human condition, and help to inhibit the diabetic human condition from progressing to a more harmful diabetes condition.

It is another objective of the present invention to provide for specific forms of certain active components.

It is another objective of the present invention to provide for compositions that help inhibit the progression of diabetis.

It the prime objective of the present invention to provide for compositions that when injested support the human endocrine system.

It is a further objective of the present invention to normalize carbohydrate metabolism.

DETAILED DESCRIPTION OF THE INVENTION

The present invention teaches a combination of specific nutrition's suitable for oral consumption by the human body. The compositions of the present invention when orally ingested on a daily basis, in combination with or without therapeutic treatments for diabetes, work to aid the diabetic patient in slowing or eliminating, or reversing the progression of the disease.

Although the mechanism of action of the compositions of the present invention are not well understood, many cases have been reported of diabetic patients benefiting from the use of the present invention.

It is believed that the key ingredients of the present invention work synergistically together to aid in the slowing, stopping, or reversing the symptoms and metabolic disorder characteristic of the human diabetic condition.

These compositions include as preferred essential component the mineral of chromium. The preferred form of chromium is yeast. The preferred amount of chromium yeast is from about 5 mcg to about 5000 mcg, and more preferred between about 100 mcg to about 2500 mcg, and most preferably from between 1000 mcg to about 2000 mcg. The preferred chromium yeast strains are *Saccharomyces cerevisiae, Saccharomyces exiguous, Saccharomyces pastorianus, Saccharomyces boulardii, Saccharomyces bayanus, Saccharomyces eubayanus, Saccharomyces florentinus, Saccharomyces fragilis*.

A prime essential ingredient included in all the embodiments of the present invention is Green Barley Juice powder. The preferred form of Green Barley Juice powder is derived from organic barley and through the process of lylyophilization of the extracted juice of the organic barley. The amount of Green Barley Juice powder 500 mg to about 3500 mg, more preferably from between 750 mg to about 2000 mg, and most preferably between 800 mg to about 1500 mg.

Inulin must be included as an essential component of the present invention. The types of Inulin to be used in the present invention include short chain, medium chain, and long chain polymers of fructoligosaccharides. The preferred amount in the present invention is from about 0.5 g to about 10.0 grams, preferably between 1 g and 7.5 g, and most preferably between 2 g and 5 g.

Another essential component is Bitter Melon. The preferred amount of Bitter Melon is from about 2 mg to about 300 mg, preferably from about 50 mg to about 250 mg, and most preferably about 100 mg to about 175 mg.

Another essential component is Erythritol. The preferred amount of Erythritol is between 1 g and 30 g, most preferably between from about 2 g-14 g.

Another essential component is Fenugreek Seed. The preferred amount of Fenugreek Seed is from about 2 mg to about 200 mg, preferably from about 50 mg to about 250 mg, and most preferably about 75 mg to about 125 mg Another essential component is Citrus Bioflavonoid. The preferred amount of Citrus Bioflavonoid is from about 2 mg to about 300 mg, preferably from about 50 mg to about 250 mg, and most preferably about 100 mg to about 175 mg Another essential component is Lime Juice Powder. The preferred amount of Lime Juice Powder is from about 1 mg to about 100 mg, preferably from about 50 mg to about 250 mg, and most preferably about 10 mg to about 75 mg.

Another essential component is Wheat Grass Juice Powder. The preferred amount of Wheat Grass Juice Powder is from about 0.5 mg to about 500 mg, preferably from about 50 mg to about 350 mg, and most preferably about 100 mg to about 275 mg These compositions may also include as preferred component the mineral of selenium. The preferred form of selenium is selenium yeast. The preferred amount of selenium yeast is from about 5 mcg to about 5000 mcg, and more preferred between about 100 mcg to about 2500 mcg, and most preferably from between 1000 mcg to about 2000 mcg. The preferred selenium yeast are *Saccharomyces cerevisiae, Saccharomyces exiguous, Saccharomyces pastorianus, Saccharomyces boulardii, Saccharomyces bayanus, Saccharomyces eubayanus, Saccharomyces florentinus, Saccharomyces fragilis.*

Another essential component of the present invention is Beta Carotene. The preferred form of beta carotene is the naturally occurring form. The preferred amount is between 10 mcg and 100 mg, and more preferably between 100 mcg and 10 mg, and most preferably between about 500 mcg and 50 mg.

Additionally, Vitamin D3 may be added to the nutritional compositions of the present invention. The preferred form of Vitamin D3 is Cholecalciferol. The preferred amount of Vitamin D3 is from between 50 iu and 3000 iu, and more preferably between from about 70 iu to about 500 iu, and most preferably from about 100 iu to about 250 iu.

Another prime nutrient that may be included in the embodiments of the present invention is Vitamin K. The preferred form of Vitamin K is Phytonadione. The preferred amount of Vitamin K is between 2.5 mcg to about 250 mcg, more preferably from between 15 mcg to about 100 mcg, and most preferably between 20 mcg to about 75 mcg.

Another nutrient important to the efficacy of the present invention is Vitamin B6. The preferred form of Vitamin B6 is Pyridoxine hydrochloride. The preferred amount is between 0.1 mg to about 100 mg, most preferably between about 0.5 mg to about 25 mg, and most preferably from about 0.75 mg to about 10 mg.

Additionally, Vitamin B12 may be included in the present invention. The preferred form of Vitamin B12 is Cyanocobalamin. The preferred amount of Vitamin B12 is between about 0.3 mcg to about 900 mcg, most preferably between about 0.75 mcg to about 50 mcg, and most preferably between 1 mcg and 10 mcg.

Another nutrient that is important to the present invention is Folic Acid. The preferred amount of Folic Acid is between about 25 mcg to about 1000 mcg, most preferably between about 100 mcg to about 750 mcg, and most preferably between 200 mcg and 400 mcg.

The mineral Zinc is important to include in the present invention. The preferred amount of Zinc is between about 0.65 mcg to about 4000 mcg, most preferably between about 1 mcg to about 400 mcg, and most preferably between 3 mcg and 50 mcg.

The mineral Molybdenum is important to include in the present invention. The preferred form of Molybdenum is from yeast. The preferred amount of Molybdenum is between about 2.5 mcg to about 1000 mcg, most preferably between about 10 mcg to about 130 mcg, and most preferably between 15 mcg and 60 mcg.

Another important nutrient is Coenzyme Q-10. The preferred amount of Coenzyme Q-10 is from about 30 mg to about 1000 mg, most preferably from between about 50 mg to 300 mg, and most preferably between about 60 mg to about 180 mg.

The following examples are illustrative only and do not limit the invention in any fashion.

EXAMPLE 1

| Ingredient | Amount | |
|---|---:|---|
| Barley Grass Juice Powder | 1250 | mg |
| Inulin | 1250 | mg |
| Chromium (from Chromium Yeast) | 50 | mcg |
| Bitter Melon Fruit | 100 | mg |
| Fenugreek Seed | 50 | mg |
| Citrus Bioflavonoid | 50 | mg |
| Lime Juice Powder | 50 | mg |
| Wheat Grass Juice Powder | 50 | mg |
| Fish Oil | 110 | mg |
| Selenium (from Selenium yeast) | 1500 | mcg |
| Beta Carotene | 200 | iu |
| Vitamin D3 | 100 | iu |
| Vitamin K | 15 | mcg |
| Vitamin B6 | 0.5 | mg |
| Vitamin B12 | 1 | mcg |
| Folic Acid | 250 | mcg |
| Zinc | 5.0 | mg |
| Molybdenum | 15 | mcg |
| CoQ-10 | 50 | mg |
| Niacin | 2.1 | mg |
| Riboflavin | 600 | mcg |
| Thiamin | 530 | mcg |
| Biotin | 2 | mg |
| Calcium | 200 | mg |
| Iron | 3 | mg |
| Phosphourous | 213 | mg |
| Iodine | 35 | mg |
| Copper | 500 | mcg |
| Manganese | 570 | mcg |
| Inositol | 1.2 | g |
| Soy Protein | 1000 | mg |
| Whey Protein Concentrate | 5000 | mg |
| Erythritol | 2500 | mg |
| Stevia Extract | 3 | mg |

The above ingredients were admixed as a single serving, and were blended together and shaken until homogeneous blend was obtained. The blended composition was poured into 250 mL of water, mixed and then consumed via drinking.

EXAMPLE 2

| Ingredient | Amount | |
|---|---:|---|
| Barley Grass Juice Powder | 1250 | mg |
| Inulin | 1250 | mg |
| Chromium (from Chromium Yeast) | 50 | mcg |
| Bitter Melon Fruit | 100 | mg |
| Fenugreek Seed | 50 | mg |
| Citrus Bioflavonoid | 50 | mg |
| Lime Juice Powder | 50 | mg |
| Wheat Grass Juice Powder | 50 | mg |
| Fish Oil | 110 | mg |
| Selenium (from Selenium yeast) | 1500 | mcg |
| Beta Carotene | 2000 | mcg |
| Ascorbic Acid | 75 | mg |
| Vitamin D3 | 100 | iu |
| Vitamin K | 15 | mcg |
| Vitamin B6 | 0.5 | mg |
| Vitamin B12 | 1 | mcg |
| Folic Acid | 250 | mcg |
| Zinc | 5.3 | mg |
| Molybdenum | 15 | mcg |
| CoQ-10 | 52 | mg |
| Niacin | 3.1 | mg |
| Riboflavin | 600 | mcg |
| Thiamin | 530 | mcg |
| Biotin | 2 | mg |
| Calcium | 200 | mg |
| Iron | 3 | mg |
| Phosphourous | 213 | mg |
| Iodine | 35 | mg |
| Copper | 500 | mcg |
| Manganese | 570 | mcg |
| Inositol | 1.2 | g |
| Potassium Iodide | 10 | mg |
| Debittered Brewers Yeast | 10 | mg |

| Ingredient | Amount |
| --- | --- |
| Copper Gluconate | 3 mg |
| Bilerry Extract | 3 mg |
| Evening Primrose Oil | 50 mg |
| Green Tea Extract | 25 mg |
| Broccoli Powder | 50 mg |
| Choline Bitartrate | 75 mg |
| Acerola Fruit Powder | 30 mg |
| Grape Juiece Concentrate | 7 mg |
| Erythritol | 2200 mg |
| Rose Hips Powder | 0.5 mg |
| Lycopene | 45 mg |
| Organic Oat Grass Juice Powder | 35 mg |
| Pine Bark Extract | 10 mg |
| Spinach Powder | 35 mg |
| Parsely Powder | 50 mg |
| Rutin | 10 mg |
| Articoke Leaf | 10 mg |
| Raspberry Fruit Powder | 50 mg |
| Lutein | 10 mg |
| Chlorella | 10 mg |
| Soy Protein | 1000 mg |
| Whey Protein Concentrate | 5000 mg |
| Natural Spearmint Flavor | 300 mg |
| Stevia Extract | 1 mg |

The above ingredients were admixed as a single serving, and were blended together and shaken until homogeneous blend was obtained. The blended composition was poured into 250 mL of water, mixed and then consumed via drinking.

EXAMPLE 3

| Ingredient | Amount |
| --- | --- |
| Barley Grass Juice Powder | 1050 mg |
| Inulin | 1420 mg |
| Chromium (from Chromium Yeast) | 75 mcg |
| Bitter Melon Fruit | 110 mg |
| Fenugreek Seed | 59 mg |
| Citrus Bioflavonoid | 43 mg |
| Lime Juice Powder | 76 mg |
| Wheat Grass Juice Powder | 72 mg |
| Fish Oil | 135 mg |
| Selenium (from Selenium yeast) | 1500 mcg |
| Beta Carotene | 300 mcg |
| Ascorbic Acid | 85 mg |
| Vitamin D3 | 200 iu |
| Vitamin K | 25 mcg |
| Vitamin B6 | 0.5 mg |
| Vitamin B12 | 1 mcg |
| Folic Acid | 230 mcg |
| Zinc | 5.8 mg |
| Molybdenum | 17 mcg |
| CoQ-10 | 62 mg |
| Niacin | 3.7 mg |
| Riboflavin | 649 mcg |
| Thiamin | 530 mcg |
| Biotin | 3 mg |
| Calcium | 200 mg |
| Iron | 3 mg |
| Phosphourous | 213 mg |
| Iodine | 35 mg |
| Copper | 500 mcg |
| Manganese | 570 mcg |
| Inositol | 1.2 g |
| Potassium Iodide | 10 mg |
| Debittered Brewers Yeast | 10 mg |
| Copper Gluconate | 3 mg |
| Bilerry Extract | 3 mg |
| Evening Primrose Oil | 50 mg |
| Green Tea Extract | 25 mg |
| Broccoli Powder | 50 mg |
| Choline Bitartrate | 75 mg |
| Acerola Fruit Powder | 30 mg |
| Grape Juiece Concentrate | 7 mg |
| Rose Hips Powder | 0.5 mg |
| Lycopene | 45 mg |
| Organic Oat Grass Juice Powder | 35 mg |
| Pine Bark Extract | 10 mg |
| Spinach Powder | 35 mg |
| Parsely Powder | 50 mg |
| Rutin | 10 mg |
| Articoke Leaf | 10 mg |
| Raspberry Fruit Powder | 50 mg |
| Lutein | 10 mg |
| Chlorella | 10 mg |
| Soy Protein | 1500 mg |
| Whey Protein Concentrate | 4000 mg |
| Natural Orange Flavor | 300 mg |
| Erythritol | 1500 mg |
| Stevia extract | 3 mg |

The above ingredients were admixed as a single serving, and were blended together and shaken until homogeneous blend was obtained. The blended composition was poured into 250 mL of water, mixed and then consumed via drinking.

EXAMPLE 4

| Ingredient | Amount |
| --- | --- |
| Barley Grass Juice Powder | 1310 mg |
| Inulin | 1600 mg |
| Chromium (from Chromium Yeast) | 200 mcg |
| Bitter Melon Fruit | 90 mg |
| Fenugreek Seed | 65 mg |
| Citrus Bioflavonoid | 1000 mg |
| Lime Juice Powder | 1000 mg |
| Wheat Grass Juice Powder | 1000 mg |
| Fish Oil | 310 mg |
| Selenium (from Selenium yeast) | 500 mcg |
| Beta Carotene | 1200 mcg |
| Ascorbic Acid | 95 mg |
| Vitamin D3 | 200 iu |
| Vitamin K | 11 mcg |
| Vitamin B6 | 1.5 mg |
| Vitamin B12 | 1.1 mcg |
| Folic Acid | 230 mcg |
| Zinc | 5.1 mg |
| Molybdenum | 17 mcg |
| CoQ-10 | 72 mg |
| Niacin | 3.1 mg |
| Riboflavin | 647 mcg |
| Thiamin | 530 mcg |
| Biotin | 3 mg |
| Calcium | 200 mg |
| Iron | 2.5 mg |
| Phosphourous | 200 mg |
| Iodine | 25 mg |
| Copper | 680 mcg |
| Manganese | 473 mcg |
| Inositol | 1.1 g |
| Potassium Iodide | 10 mg |
| Debittered Brewers Yeast | 10 mg |
| Copper Gluconate | 3 mg |
| Bilerry Extract | 3 mg |
| Evening Primrose Oil | 50 mg |
| Green Tea Extract | 25 mg |
| Broccoli Powder | 50 mg |
| Choline Bitartrate | 75 mg |
| Acerola Fruit Powder | 30 mg |
| Grape Juiece Concentrate | 7 mg |
| Rose Hips Powder | 0.5 mg |
| Lycopene | 45 mg |

| Ingredient | Amount |
| --- | --- |
| Erythritol | 2500 mg |
| Organic Oat Grass Juice Powder | 35 mg |
| Pine Bark Extract | 10 mg |
| Spinach Powder | 35 mg |
| Parsely Powder | 50 mg |
| Rutin | 10 mg |
| Articoke Leaf | 10 mg |
| Raspberry Fruit Powder | 50 mg |
| Lutein | 10 mg |
| Chlorella | 10 mg |
| Soy Protein | 1000 mg |
| Whey Protein Concentrate | 5000 mg |
| Natural Spearmint Flavor | 300 mg |
| Stevia Extract | 100 mcg |

The above ingredients were admixed as a single serving, and were blended together and shaken until homogeneous blend was obtained. The blended composition was poured into 250 mL of water, mixed and then consumed via drinking.

EXAMPLE 5

| Ingredient | Amount |
| --- | --- |
| Barley Grass Juice Powder | 2550 mg |
| Inulin | 850 mg |
| Chromium (from Chromium Yeast) | 1200 mcg |
| Bitter Melon Fruit | 200 mg |
| Fenugreek Seed | 39 mg |
| Citrus Bioflavonoid | 80 mg |
| Lime Juice Powder | 90 mg |
| Wheat Grass Juice Powder | 90 mg |
| Fish Oil | 310 mg |
| Selenium (from Selenium yeast) | 500 mcg |
| Beta Carotene | 100 mcg |
| Ascorbic Acid | 500 mg |
| Vitamin D3 | 100 iu |
| Vitamin K | 15 mcg |
| Vitamin B6 | 0.5 mg |
| Vitamin B12 | 1 mcg |
| Folic Acid | 250 mcg |
| Zinc | 5.3 mg |
| Molybdenum | 15 mcg |
| CoQ-10 | 52 mg |
| Niacin | 3.1 mg |
| Riboflavin | 300 mcg |
| Thiamin | 130 mcg |
| Erythritol | 2500 mg |
| Biotin | 1 mg |
| Calcium | 400 mg |
| Iron | 3 mg |
| Phosphourous | 220 mg |
| Iodine | 37 mg |
| Copper | 510 mcg |
| Manganese | 524 mcg |
| Inositol | 1.1 g |
| Potassium Iodide | 10 mg |
| Debittered Brewers Yeast | 10 mg |
| Copper Gluconate | 3 mg |
| Bilerry Extract | 3 mg |
| Evening Primrose Oil | 50 mg |
| Green Tea Extract | 25 mg |
| Broccoli Powder | 50 mg |
| Choline Bitartrate | 75 mg |
| Acerola Fruit Powder | 30 mg |
| Grape Juiece Concentrate | 7 mg |
| Rose Hips Powder | 0.5 mg |
| Lycopene | 45 mg |
| Organic Oat Grass Juice Powder | 35 mg |
| Pine Bark Extract | 10 mg |
| Spinach Powder | 35 mg |
| Parsely Powder | 50 mg |
| Rutin | 10 mg |
| Articoke Leaf | 10 mg |
| Raspberry Fruit Powder | 50 mg |
| Lutein | 10 mg |
| Chlorella | 10 mg |
| Soy Protein | 1000 mg |
| Whey Protein Concentrate | 5000 mg |

What is claimed is:

1. An orally administered composition comprising Chromium, Green Barley Juice Powder, Bitter Melon, Inulin, Erythritol, Fenugreek Seed, Lime Juice concentrate, Citrus Bioflavonoid, Beta Carotene, Wheat Grass Juice Powder, Selenium, Vitamin D, Vitamin K, Vitamin B12, Vitamin C, Folic Acid, Zinc, Molybdenum, and Coenzyme Q-10, wherein selenium is provided as selenium yeast.

2. The composition of claim 1 wherein the amount of Chromium is between 5 mcg and 5 mg per serving.

3. The composition of claim 1 having amounts of Green Barley Juice Powder between 500 mg to about 3500 mg per serving.

4. The composition of claim 1 wherein the amount of Inulin is between 0.5 g to about 10.0 grams per serving.

5. The composition of claim 1 wherein the amount of Bitter Melon is between 2 mg and 300 mg per serving.

6. The composition of claim 1 wherein the amount of Erythritol is between 2 g-14 g per serving.

7. The composition of claim 1 wherein the amount of Fenugreek Seed is 2 mg to about 200 mg per serving.

8. The composition of claim 1 wherein the amount of Citrus Bioflavonoid is from 2 mg to about 300 mg per serving.

9. The composition of claim 1 wherein the amount of Lime Juice Powder is from 50 mg to about 250 mg per serving.

10. The composition of claim 1 wherein the amount of Wheat Grass Juice Powder is from 0.5 mg to about 500 mg per serving.

11. The composition of claim 1 wherein the amount of Selenium is between 5 mcg and 5000 mcg per serving.

12. The composition of claim 1 wherein the amount of Beta Carotene is from 10 mcg to 100 mg per serving.

13. The composition of claim 1 wherein the Vitamin D is Vitamin D3, and wherein the amount of Vitamin D3 is between 50 iu and 3000 iu per serving.

14. The composition of claim 1 wherein the amount of Vitamin K is between 25 mcg to about 250 mcg per serving.

15. The composition of claim 1 further comprising Vitamin B6 in an amount between 0.1 mg to about 100 mg per serving.

16. The composition of claim 1 wherein the amount of Folic Acid is between 25 mcg to about 1000 mcg.

17. The composition of claim 1 wherein the amount of Zinc is between about 0.65 mcg to about 4000 mcg per serving.

18. The composition of claim 1 wherein the amount of Molybdenum is between 2.5 mcg to about 1000 mcg.

19. The composition of claim 1 wherein the amount of Coenzyme Q-10 is between 30 mg to about 1000 mg.

* * * * *